United States Patent [19]

Sakaguchi et al.

[11] Patent Number: 4,897,540

[45] Date of Patent: Jan. 30, 1990

[54] APPARATUS FOR DETECTING THE PRESENCE OR ABSENCE OF OVERLAP AT TAPE JOINTS

[75] Inventors: Masaaki Sakaguchi; Kazuo Kubota, both of Kanagawa, Japan

[73] Assignee: Fuji Photo Film Co., Ltd., Kanagawa, Japan

[21] Appl. No.: 211,645

[22] Filed: Jun. 27, 1988

[30] Foreign Application Priority Data

Jul. 1, 1987 [JP] Japan ................................ 62-164690

[51] Int. Cl.$^4$ ............................................. G01N 9/04
[52] U.S. Cl. ................................. 250/223 R; 250/570; 356/430
[58] Field of Search ............... 250/561, 571, 223 R, 250/570; 356/237–239, 429–431

[56] References Cited

U.S. PATENT DOCUMENTS

| | | | |
|---|---|---|---|
| 3,856,414 | 12/1974 | Menary | 250/570 |
| 4,237,378 | 12/1980 | Jones | 250/223 R |
| 4,286,149 | 8/1981 | Ben-Nathan et al. | 250/223 R |
| 4,525,630 | 6/1985 | Chapman | 250/572 |
| 4,611,907 | 9/1986 | Inatsuki | 250/571 |

Primary Examiner—David C. Nelms
Assistant Examiner—Stephone B. Allen
Attorney, Agent, or Firm—Sughrue, Mion, Zinn, Macpeak & Seas

[57] ABSTRACT

A joint inspection apparatus comprises a light irradiating device for irradiating light to a tape joint at which two tape edge portions are joined together, and a light receiving device for receiving the light irradiated by the light irradiating device to the tape joint and passing through the tape joint or reflected by the tape joint. A judgment device is provided for judging the presence or absence of an overlap of the two tape edge portions one upon the other at the tape joint on the basis of information on the optical amount of the light received by the light receiving device in the vicinity of the tape joint.

5 Claims, 3 Drawing Sheets

APPARATUS FOR DETECTING THE PRESENCE OR ABSENCE OF OVERLAP AT TAPE JOINTS

BACKGROUND OF THE INVENTION

1. Field of the Invention

This invention relates to a joint inspection apparatus for automatically inspecting an overlap of tape edge portions one upon the other at a tape joint in the case where long tapes are joined together. This invention particularly relates to a joint inspection apparatus for detecting the presence or absence of an overlap of edge portions of, for example, a leader tape and a magnetic tape one upon the other, which overlap may arise in the case where the leader tape and the magnetic tape are joined together by use of a joining tape for obtaining a video tape, an audio tape or the like.

2. Description of the Prior Art

In the course of making video tape cassettes or audio tape cassettes, a leader tape (or a trailer tape) and a magnetic tape are joined together by use of a joining tape, and the presence or absence of an overlap of edge portions of the leader tape and the magnetic tape one upon the other at the joint area has heretofore been judged by visual inspection by the operators.

However, with the visual inspection, criteria of judgment differ among the operators, and defective products may be missed due to fatigue of the operators. Therefore, it is not always possible to make the quality of the products uniform. Also, personnel expenses for the operators cause the product cost to increase, and the production speed is decreased by the presence of the artificial process in the production processes.

SUMMARY OF THE INVENTION

The primary object of the present invention is to provide a joint inspection apparatus for automatically detecting the presence or absence of an overlap of tape edge portions one upon the other at a tape joint, thereby to make the quality of tape products uniform.

Another object of the present invention is to provide a joint inspection apparatus which enables reduction in the tape product cost and an increase in the tape production speed.

The present invention provides a joint inspection apparatus comprising:

(i) a light irradiating means for irradiating light to a tape joint at which two tape edge portions are joined together, (ii) a light receiving means for receiving the light irradiated by said light irradiating means to said tape joint and passing through said tape joint or reflected by said tape joint, and (iii) a judgment means for judging the presence or absence of an overlap of said two tape edge portions one upon the other at said tape joint on the basis of information on the optical amount of the light received by said light receiving means in the vicinity of said tape joint.

The term "tape joint" as used herein means the joint area formed when two tape edge portions are joined together.

The light receiving means may be composed of, for example, a single photo-transistor or a plurality of photo-transistors, a line sensor or a surface sensor. In the case where the light receiving means is composed of a single photo-transistor or a plurality of photo-transistors disposed in the tape width direction, or a line sensor extending in the tape width direction, it is necessary to move the tape joint with respect to the light irradiating means and the light receiving means in the tape length direction for sequentially obtaining the information on the optical amount in the vicinity of the tape joint. On the other hand, in the case where the light receiving means is composed of a surface sensor such as a charge coupled device (CCD) or the like, the tape joint may be maintained stationary with respect to the light irradiating means and the light receiving means. In this case, it is necessary to cause the light obtained at different portions of the area in the vicinity of the tape joint to impinge upon the surface sensor simultaneously or substantially simultaneously, and then sequentially obtain the information on the optical amount over the overall surface of the surface sensor by electronic scanning.

With the joint inspection apparatus in accordance with the present invention, the presence or absence of an overlap of the tape edge portions one upon the other at the tape joint is automatically determined on the basis of the information on the optical amount on both sides of the tape joint obtained by receiving the light irradiated to the tape joint and passing through the tape joint or reflected by the tape joint. Therefore, the quality of the tape products can be judged objectively and reliably based on the results of the determination, and the quality of the products can be made uniform. Also, with the determination by the automatic detection, the presence or absence of an overlap of the tape edge portions one upon the other at the tape joint is automatically judged instantaneously by the light detection and processing of the electric signals, and the production speed can be increased since the inspection efficiency is not caused to decrease by fatigue of the operators as in the case of visual inspection. Moreover, with the joint inspection apparatus in accordance with the present invention which has the simple configuration and which can be fabricated at a low cost, the tape production cost can be decreased as compared with the case where personnel expenses are required for the operators engaging in visual inspection.

DESCRIPTION OF THE PREFERRED EMBODIMENTS

The present invention will hereinbelow be described in further detail with reference to the accompanying drawings.

Figure 1:
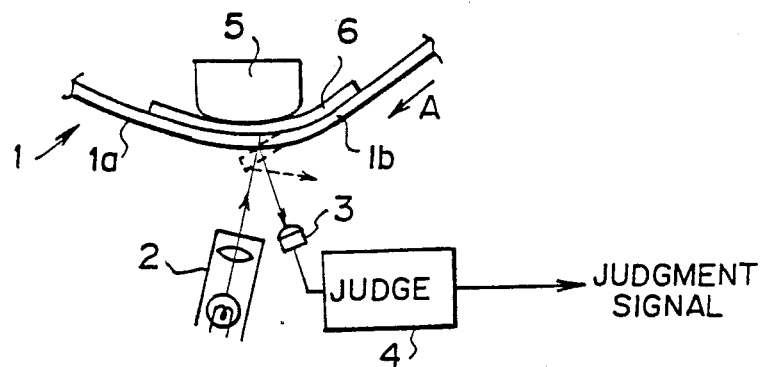
FIG. 1 is a schematic view showing an embodiment of the joint inspection apparatus in accordance with the present invention.

With reference to FIG. 1, an embodiment of the joint inspection apparatus in accordance with the present invention comprises a light irradiating means 2 for irradiating a light beam to a tape 1 moved in the direction as indicated by the arrow A between two reels (not shown), a light receiving means 3 for receiving the light beam irradiated by the light irradiating means 2 to the tape 1 and reflected by the tape 1, and a judgment means 4 for inspecting the presence or absence of an overlap of tape edge portions of a leader tape 1a and a magnetic tape 1b one upon the other at the tape joint on the basis of information on the optical amount of the light beam received by the light receiving means 3, and generating a judgment signal indicating that the product is defective in the case where the overlap is detected. Also, a backup head 5 is disposed on the side opposite to the light irradiating means 2 with respect to the tape 1 in the vicinity of the position at which the light produced by the light irradiating means 2 impinges upon the tape 1.

A known motor capable of achieving constant speed movement of the tape 1 is employed as the tape movement mechanism. As the loading and unloading mechanism for the backup head 5, by way of example, a cylinder mechanism is employed.

Operations of judging the presence or absence of an overlap of the tape edge portions one upon the other at the tape joint by use of this embodiment will be described hereinbelow.

The two reels are rotated to move the tape 1 at a constant speed of approximately 20 mm/sec in the direction as indicated by the arrow A between the two reels. At the same time, the light beam is irradiated by the light irradiating means 2 onto the tape 1. The backup head 5 is disposed in advance to contact the tape 1 at the back of the tape area upon which the light beam impinges. The light receiving means 3 is provided so that its light receiving face receives the light beam reflected by the tape 1. Also, the information on the optical amount of the light beam reflected by the tape 1 and received by the light receiving means 3 is sequentially fed as electric signals to the judgment means 4.

The tape 1 has been formed by joining the edge portion of the leader tape 1a and the edge portion of the magnetic tape 1b together by use of a joining tape 6. The edge portions of the leader tape 1a and the magnetic tape 1b have edge faces cut normal to the direction of tape movement. Therefore, in the case where the leader tape 1a and the magnetic tape 1b have been joined together accurately, the edge portions of the leader tape 1a and the magnetic tape 1b are in abutment with and joined to each other without a gap intervening therebetween. However, actually, it is not always possible to adjust the positions of the leader tape 1a and the magnetic tape 1b accurately in the course of the joining, so that the joining accuracy fluctuates and an overlap of the edge portions of the leader tape 1a and magnetic tape 1b one upon the other often arises at the tape joint. Such an overlap deteriorates the quality of the tape product, and therefore delivery of such a tape product to the market must be avoided.

Figure 2:
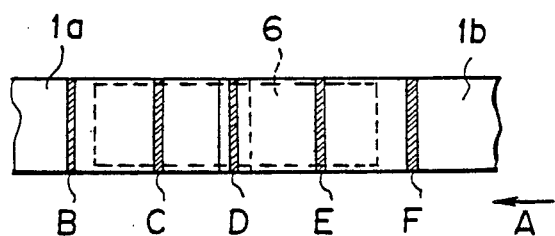
FIG. 2 is a schematic view showing irradiation of light produced by the light irradiating means to the area in the vicinity of a tape joint.

Accordingly, the aforesaid embodiment is constituted for automatically judging the presence or absence of an overlap of the tape edge portions one upon the other, and discriminating the quality of the product. Specifically, in the course of inspection of the tape 1 having an overlap of the tape edge portions one upon the other as shown in FIG. 2, at the time the tape 1 is moved and a linear region B on the tape 1 arrives at the light beam irradiating position, the information on the optical amount of the light beam reflected by the linear region B is fed to the judgment means 4 via the light receiving means 3. At the time the tape 1 is further moved in the direction as indicated by the arrow A and linear regions C, D, E and F on the tape 1 sequentially arrives at the light beam irradiating position, the information on the optical amounts of the light beam reflected by the linear regions C, D, E and F is sequentially fed to the judgment means 4 via the light receiving means 3.

Figure 3:
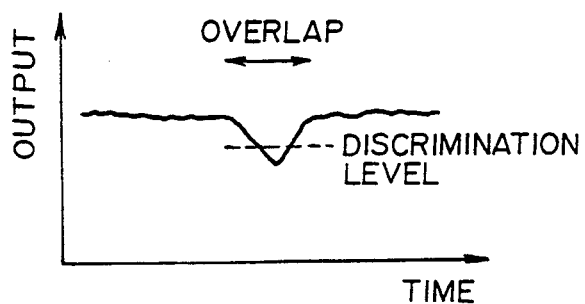
FIG. 3 is a graph showing the output of the light receiving means in the embodiment shown in FIG. 1.

The light receiving means 3 is composed of two light receiving elements (photodiodes, photo-transistors, photomultipliers or the like) disposed side by side in the tape width direction. The reason for this is that, with a single light receiving element, it is not always possible to judge accurately in the case where the edge portions of the leader tape 1a and the magnetic tape 1b are joined together in a "<" condition such that they overlap at a part and are spaced from each other at the other part. Therefore, in this embodiment, the outputs of the two light receiving elements are added together to obtain the output of the light receiving means 3. In accordance with the light receiving elements, the light irradiating means 2 should preferably be constituted by a light source such as a laser capable of converging the light beam to a beam diameter within the range of 0.1 mm to 0.2 mm. FIG. 3 shows a graph wherein the time is plotted on the horizontal axis and the level of the output of the light receiving means 3 is plotted on the vertical axis. As shown in FIG. 3, the optical amount of the light beam reflected by the tape 1 decreases sharply at the area where the edge portions of the leader tape 1a and the magnetic tape 1b overlap one upon the other. Specifically, in the case where the leader tape 1a and the magnetic tape 1b are accurately joined together at the tape joint, the light beam reflected by the tape joint impinges upon the light receiving face of the light receiving means 3 as in the case of the light beam irradiated onto the ordinary surface of the tape 1 and reflected thereby. In contrast, in the case where an overlap of the edge portions of the leader tape 1a and the magnetic tape 1b one upon the other is present at the tape joint as indicated by the broken line in FIG. 1, the angle of incidence of the light beam upon the tape surface at the overlap region changes because of the inclination of the tape surface at the overlap region, the angle of reflection of the light beam also changes, and the optical amount of the light beam reflected and incident upon the light receiving means 3 decreases. Therefore, the judgment means 4 compares the level of the output with a reference value at the area provided with the joining tape 6, and judges that an overlap is present when the level of the output is not higher than the reference value.

Figure 4:
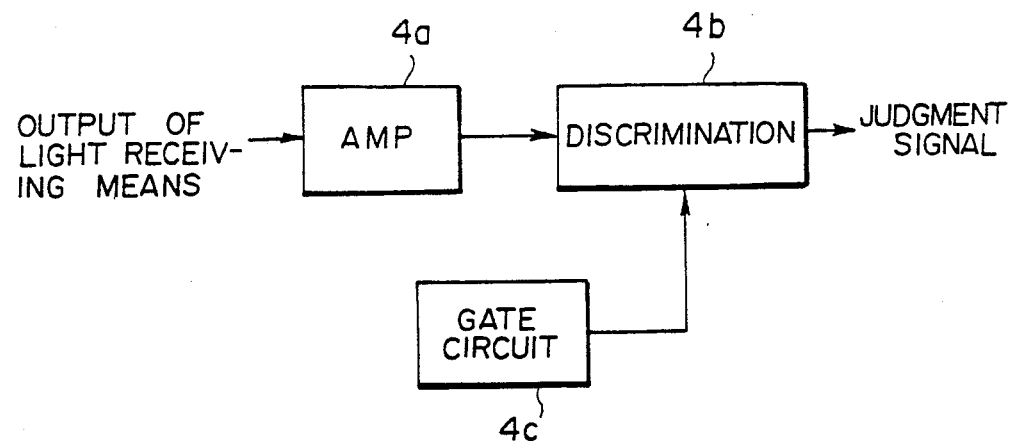
FIG. 4 is a block diagram showing the judgment means in the embodiment shown in FIG. 1, and FIGS. 5 and 6 are schematic views showing a part of further embodiments of the joint inspection apparatus in accordance with the present invention.

FIG. 4 is a block diagram showing the configuration of the judgment means 4 in detail. The output signal generated by the light receiving means 3 is amplified by an amplifying circuit 4a and fed to a discrimination circuit 4b. The discrimination circuit 4b compares the level of the output signal received from the amplifying circuit 4a with a predetermined discrimination level. Also, a gate circuit 4c feeds a gate signal to the discrimination circuit 4b so that the discrimination is carried out only in the vicinity of the tape joint. The timing of gate signal feed start may be adjusted so that the gate signal is fed a predetermined period after the detection of the overlapping of the leader tape 1a upon the joining tape 6. Alternatively, the position of the tape joint may be adjusted in advance, and the gate signal may be fed after a predetermined predicted time has elapsed. The discrimination circuit 4b outputs an OK signal in the case where the minimum level of the output signal received from the amplifying circuit 4a is found to be higher than the discrimination level, and outputs a NG signal in the case where said minimum level is found to be lower than the discrimination level.

The judgment signal may be fed to a buzzer so that a warning is issued for a predetermined period in the case where the NG signal is generated. Also, light emitting diodes may be provided on a control panel for visibly indicating the OK signal and the NG signal generated as the judgment signal. This method is advantageous for sorting of the products.

In the aforesaid embodiment, the tape 1 and the backup head 5 are disposed so that the tape 1 slides along the backup head 5. However, they need not necessarily be disposed so that the tape 1 slides along the backup head 5. Also, instead of adding the outputs of the two light receiving elements to each other to obtain the output of the light receiving means 3, the outputs of the two light receiving elements may be processed by independent discrimination circuits.

Figure 6:
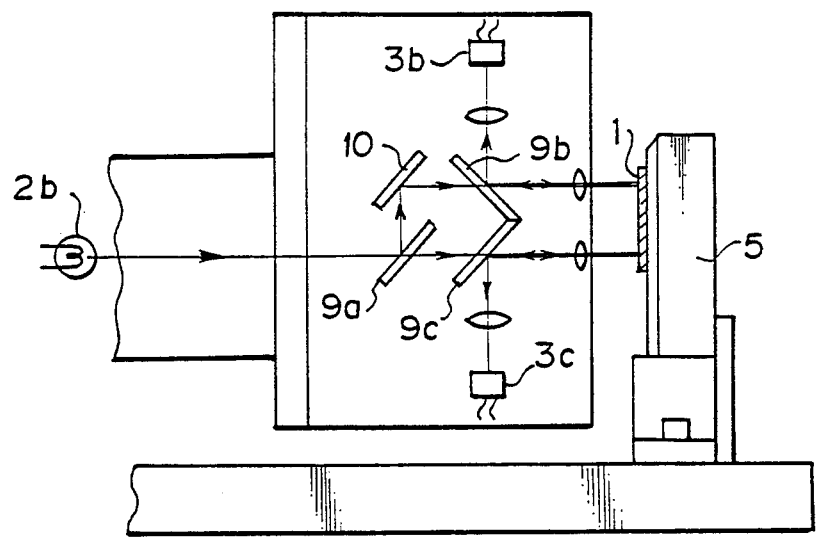

In the case where the light beam is irradiated normal to the tape surface, the optical axis of the irradiated light beam and the optical axis of the reflected light beam coincide with each other. In this case, a light irradiating means 2b and light receiving means 3b and 3c may be disposed as shown in FIG. 6. With reference to FIG. 6, the tape 1 is moved at an angle normal to the drawing sheet in FIG. 6, and light beams are irradiated to two positions standing side by side in the tape width direction by use of a semi-transparent mirror 9a and a mirror 10. The light beams reflected by the tape 1 are made to impinge upon light receiving elements 3b and 3c by use of semi-transparent mirrors 9b and 9c.

In the aforesaid embodiments, the tape 1 before being housed in a cassette is inspected. However, also after the tape is housed in a cassette, inspection can be carried out in the same manner by opening and closing a guard panel.

Also, in the aforesaid embodiments, the information on the optical amount is obtained by receiving the light beam reflected by the tape 1. However, in the case where the leader tape 1a and the magnetic tape 1b are light-permeable to some extent, the joint inspection apparatus in accordance with the present invention may be constituted to obtain the information on the optical amount by receiving a light beam passing through the tape 1. In this case, the optical amount of the light beam passing through the tape 1 decreases at an overlap of the edge portions of the leader tape 1a and the magnetic tape 1b, and therefore the presence or absence of the overlap may be judged by determining a change in the optical amount of the light beam passing through the tape 1.

In the aforesaid embodiments, the information on the optical amount of the light beam obtained at respective regions on the tape 1 is obtained by securing the light irradiating means 2 and the light receiving means 3 and moving the tape 1. Instead, the information on the optical amount of the light beam obtained at respective regions on the tape 1 may be obtained by moving the light irradiating means 2 and the light receiving means 3 in the tape length direction. Alternatively, the light receiving means 3 may be constituted by a surface sensor such as a CCD, and the light irradiating means 2, the light receiving means 3 and the tape joint may be disposed at such positions that the light beam irradiated onto the area in the vicinity of the tape joint and reflected by said area or passing through said area simultaneously impinges upon the surface sensor. Then, the quality of the tape product may be judged in the same manner as in the aforesaid embodiments on the basis of the information on the optical amount generated by the surface sensor.

Also, a second light receiving means may be provided on the side opposite to the light irradiating means 2 with respect to the tape 1 so that the light beam passing through the tape 1 impinges upon the second light receiving means, and the size of a gap between the two tape edge portions at the tape joint may be detected on the basis of the optical amount information obtained as the output of the second light receiving means. In this case, it is possible to detect an overlap of the edge portions of the leader tape 1a and the magnetic tape 1b one upon the other at the tape joint, and the gap between said edge portions.

Figure 5:
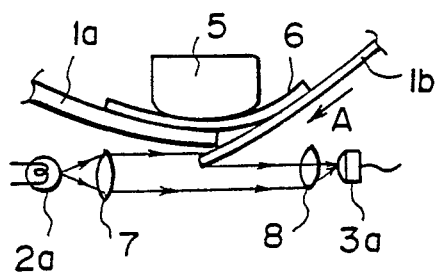

Moreover, as shown in FIG. 5, a light irradiating means 2a and a light receiving means 3a may be disposed so that the straight line (optical axis) on which the light irradiating means 2a and a light receiving means 3a lie is approximately parallel to the direction of movement of the tape, and a part of the light beam is intercepted by a tape edge portion in the case where an overlap of tape edge portions is present at the tape joint. An optical system 7 for collimating the light beam is disposed at the rear of the light irradiating means 2a, and an optical system 8 for converging the collimated light beam is disposed in front of the light receiving means 3a. With the embodiment shown in FIG. 5, in the case where an overlap of the tape edge portions is present, the optical amount of the light beam which the light receiving means 3a receives decreases, and the level of the output of the light receiving means 3a becomes low. Therefore, based on a change in the optical amount, the presence or absence of an overlap can be judged by the discrimination circuit 4b as shown in FIG. 4. In general, the sum of the thicknesses of the leader tape 1a and the magnetic tape 1b is approximately 40 $\mu$m. Actually, however, the thickness at the overlap is within the range of 40 $\mu$m to 200 $\mu$m because of floating of the tape edge portion at the overlap, and the overlap can be detected comparatively easily.

We claim:

1. A joint inspection apparatus for determining whether or not first and second tapes are joined at respective edge portions without overlap, the apparatus comprising:
   (i) a light irradiating means for irradiating light normal to the direction of the movement of a tape joint at which said respective edge portions are joined together,
   (ii) a light receiving means for receiving the light irradiated by said light irradiating means to said tape joint and passing through said tape joint or reflected by said tape joint, and
   (iii) a judgment means for judging the presence or absence of an overlap of said respective tape edge portions one upon the other at said tape joint on the basis of information on the optical amount of the light received by said light receiving means in the vicinity of said tape joint, said judgment means including a discrimination circuit which compares the level of an amplified output signal generated by said light receiving means with a predetermined discrimination level indicative of the presence of overlap.

2. An apparatus as defined in claim 1 wherein said light irradiating means is constituted by a laser.

3. An apparatus as defined in claim 1, wherein said judgment means is connected to a warning means comprising means for producing at least one of an audible or visible signal for issuing a warning at the time the overlap is detected.

4. An apparatus as defined in claim 1, wherein said light beam is irradiated at two different positions along a width of the tape, said light irradiating means comprising a semi-transparent mirror and a mirror, and further wherein said light receiving means is adapted for reception of said light beams reflected by different positions at said tape joint in the tape width direction.

5. An apparatus as defined in claim 1, wherein said judgment means further comprises a gate circuit for applying a gate signal to said judgment means to cause said judgment means to effect said comparing only in the vicinity of said tape joint.

* * * * *